United States Patent
Henry et al.

(10) Patent No.: US 12,082,905 B2
(45) Date of Patent: Sep. 10, 2024

(54) TREATING EPILEPSY AND OTHER NEUROLOGICAL DISORDERS BY TARGETING THERAPY TO THE ENDOPIRIFORM NUCLEUS USING ULTRA-HIGH FIELD MAGNETIC RESONANCE IMAGING

(71) Applicant: REGENTS OF THE UNIVERSITY OF MINNESOTA, Minneapolis, MN (US)

(72) Inventors: Thomas R. Henry, Minneapolis, MN (US); Gregory F. Molnar, Minneapolis, MN (US); Michael C. Park, Minneapolis, MN (US); Pierre-Francois Van De Moortele, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 72 days.

(21) Appl. No.: 17/766,420

(22) PCT Filed: Oct. 5, 2020

(86) PCT No.: PCT/US2020/054247
§ 371 (c)(1),
(2) Date: Apr. 4, 2022

(87) PCT Pub. No.: WO2021/067928
PCT Pub. Date: Apr. 8, 2021

(65) Prior Publication Data
US 2023/0190105 A1    Jun. 22, 2023

Related U.S. Application Data

(60) Provisional application No. 62/910,798, filed on Oct. 4, 2019.

(51) Int. Cl.
A61B 5/00 (2006.01)
A61N 1/36 (2006.01)

(52) U.S. Cl.
CPC .......... *A61B 5/0042* (2013.01); *A61B 5/0036* (2018.08); *A61N 1/36064* (2013.01)

(58) Field of Classification Search
CPC .. A61B 5/0036; A61B 5/0042; A61N 1/36064
See application file for complete search history.

(56) References Cited

U.S. PATENT DOCUMENTS 11,324,413 B1 * 5/2022 Benson .............. G01R 33/5602
2014/0249396 A1    9/2014 Shacham-Diamand et al.
(Continued)

OTHER PUBLICATIONS

Nagaraj, Vivek. Optimizing Electrical Brain Stimulation for Seizure Disorders, University of Minnesota, Mar. 2017, https://conservancy.umn.edu/handle/11299/188920. Accessed Oct. 27, 2023. (Year: 2017).*

(Continued)

*Primary Examiner* — Gregory H Curran
(74) *Attorney, Agent, or Firm* — QUARLES & BRADY LLP

(57) ABSTRACT

Ultra-high field ("UHF") magnetic resonance imaging ("MRI") is used to localize the endopiriform nucleus ("EPN") as a target for neuromodulation treatment. Single or multiple different image contrasts can be used to guide localization of the EPN. Treatment plan data are generated based on the localized EPN, and may include coordinate data, trajectory data, or both, for delivering neuromodulation treatment to the localized EPN.

27 Claims, 5 Drawing Sheets

(56) References Cited

U.S. PATENT DOCUMENTS

2019/0090749 A1* 3/2019 Leuthardt ............. G06T 7/0012
2021/0311076 A1* 10/2021 Kipnis ................... A61B 5/055

OTHER PUBLICATIONS

Behan et al., "Intrinsic and efferent connections of the endopiriform nucleus in rat," J Comp Neurol, 408: 532-548, May 1999.

Bergey et al., "Long-term treatment with responsive brain stimulation in adults with refractory partial seizures," Neurology 84(8):810-7, Feb. 2015.

Van De Moortele et al. "T1 weighted brain images at 7 Tesla unbiased for Proton Density, T2* contrast and RF coil receive B1 sensitivity with simultaneous vessel visualization," Neuroimage 46:432-446, Jun. 2009.

Wojcik et al., "Analysis of calcium binding protein immunoreactivity in the claustrum and the endopiriform nucleus of the rabbit," Acta Neurobiol. Exp. 64: 449-460, Apr. 2004.

Majak et al., "Endopiriform nucleus connectivities: the implications for epileptogenesis and epilepsy," Folia Morphol (Warsz); 66(4):267-71, Dec. 2007.

PCT International Search Report and Written Opinion Application: PCT/US2020/054247 Jan. 8, 2021, 8 pages.

* cited by examiner

TREATING EPILEPSY AND OTHER NEUROLOGICAL DISORDERS BY TARGETING THERAPY TO THE ENDOPIRIFORM NUCLEUS USING ULTRA-HIGH FIELD MAGNETIC RESONANCE IMAGING

CROSS-REFERENCE TO RELATED APPLICATIONS

This application is a U.S. 371 national phase patent application based on International Patent Application No. PCT/US2020/054247, filed on Oct. 5, 2020 and published on Apr. 8, 2021 as International Publication Number WO 2021/067928 A1, which claims the benefit of U.S. Provisional Patent Application Ser. No. 62/910,798, filed on Oct. 4, 2019 and entitled "TREATING EPILEPSY AND OTHER NEUROLOGICAL DISORDERS BY TARGETING THERAPY TO THE ENDOPIRIFORM NUCLEUS USING ULTRA-HIGH FIELD MAGNETIC RESONANCE IMAGING," all of which are herein incorporated by reference in their entireties for all purposes.

STATEMENT REGARDING FEDERALLY SPONSORED RESEARCH

This invention was made with government support under RR008079 and NS057091 awarded by the National Institutes of Health. The government has certain rights in the invention.

BACKGROUND

Approximately one-third of patients with epilepsy do not achieve freedom from seizures using anti-seizure medications. A minority of drug-refractory epilepsy patients can safely undergo epilepsy surgery with ablative and/or resective procedures that destroy brain tissue and brain lesions to fully control seizures, although many patients who undergo ablative and/or resective procedures have some residual seizures after surgery. Further, many candidates for ablative and/or resective epilepsy surgery are found to have eloquent cortex at the site (s) where electrical seizures begin, such that ablation and/or resection of this essential cortex would be expected to produce permanent motor, sensory, language, memory, cognitive, or other functional impairments. Ablative and/or resective surgery is not performed when disabling impairments of these types are expected to occur, and also is not considered safe to perform when seizures originate in multiple brain structures in a single individual.

Electrical stimulation of neural structures can be performed to interfere with seizure generation in drug-refractory epilepsy patients, without ablation of neural tissue. Current clinical practice includes three types of neural electrical stimulation using FDA-approved devices in epilepsy: (1) vagus nerve stimulation, (2) direct stimulation of cerebral ictal onset zones with responsive neural stimulation, and (3) anterior nucleus of the thalamus deep brain stimulation. There still remains unmet need to treat patients and each of the techniques has its therapeutic and technological shortcomings.

Each of the aforementioned types of FDA-approved devices used for neural electrical stimulation in epilepsy is based on a different mechanistic model for seizure attenuation. Vagus nerve stimulation ("VNS") is thought to antagonize seizures by stimulating afferent vagal projections to the nucleus tractus solitarius and other medullary sites with polysynaptic activation of the thalamus bilaterally, serving to modulate epileptic excitability in widespread cortical regions. Responsive neural stimulation ("RNS") is designed to electrically stimulate the site(s) of ictal onset, at times of initial electrographic seizure discharges or pre-seizure EEG changes as recorded with the stimulating electrodes, using automated EEG analysis components of the pulse generator system. Anterior nucleus of the thalamus deep brain stimulation ("ANT-DBS") is thought to act in a neuromodulatory fashion to reduce cortical epileptic excitability by effects on the anterior nuclei of the thalamus, which are known to have dense projections to multiple cortical sites where seizure onset can occur, probably by desynchronizing transsynaptic activities at the sites of seizure onset. Long-term follow-up of epilepsy patients treated with each of these neural stimulation devices has shown significant long-term seizures reductions, but fewer than 20% of patients achieve complete seizure control with any of these devices.

Thus, there remains a need for treatment strategies that are capable of more effectively reducing seizures in patients.

SUMMARY OF THE DISCLOSURE

The present disclosure addresses the aforementioned drawbacks by providing systems and methods for generating treatment plan data from images acquired using a magnetic resonance imaging ("MRI") system. Magnetic resonance image data acquired from a subject using an ultra-high field MRI system are accessed with a computer system. The magnetic resonance image data includes at least T2-weighted images of the subject. The subject's endopiriform nucleus ("EPN") is localized by using the computer system to analyze the T2-weighted images, generating output as localized EPN data. Treatment plan data are then generated with the computer system based on at least the localized EPN data. The treatment plan data define a treatment delivery for delivering treatment to the subject's EPN. A therapy system is also provided that can receive the EPN data and/or treatment plan based on the EPN data to effectuate a therapy.

It is another aspect of the present disclosure to provide a neuromodulation device for implant in a brain of a subject, which includes a pulse generator, a controller, and an electrical lead. The pulse generator is configured to generate electrical pulses that are configured to be delivered the brain of the subject. The controller is coupled to receive data from a plurality of sources. The received data include at least one of localized EPN data or a treatment plan generated from EPN data. The controller is also configured to control the pulse generator to generate electrical pulses to effectuate a therapy that will control seizures in the subject. These electrical pulses are generated using the EPN data, where the EPN data are formed from T2-weighted MRI images of the brain of the subject. The electrical lead includes a distal-end region having a plurality of electrodes configured to extend into the brain of the subject to deliver the electrical pulses generated by the pulse generator and a proximal-end region having a lead interface configured to mechanically and electrically couple to and subsequently decouple from the pulse generator.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
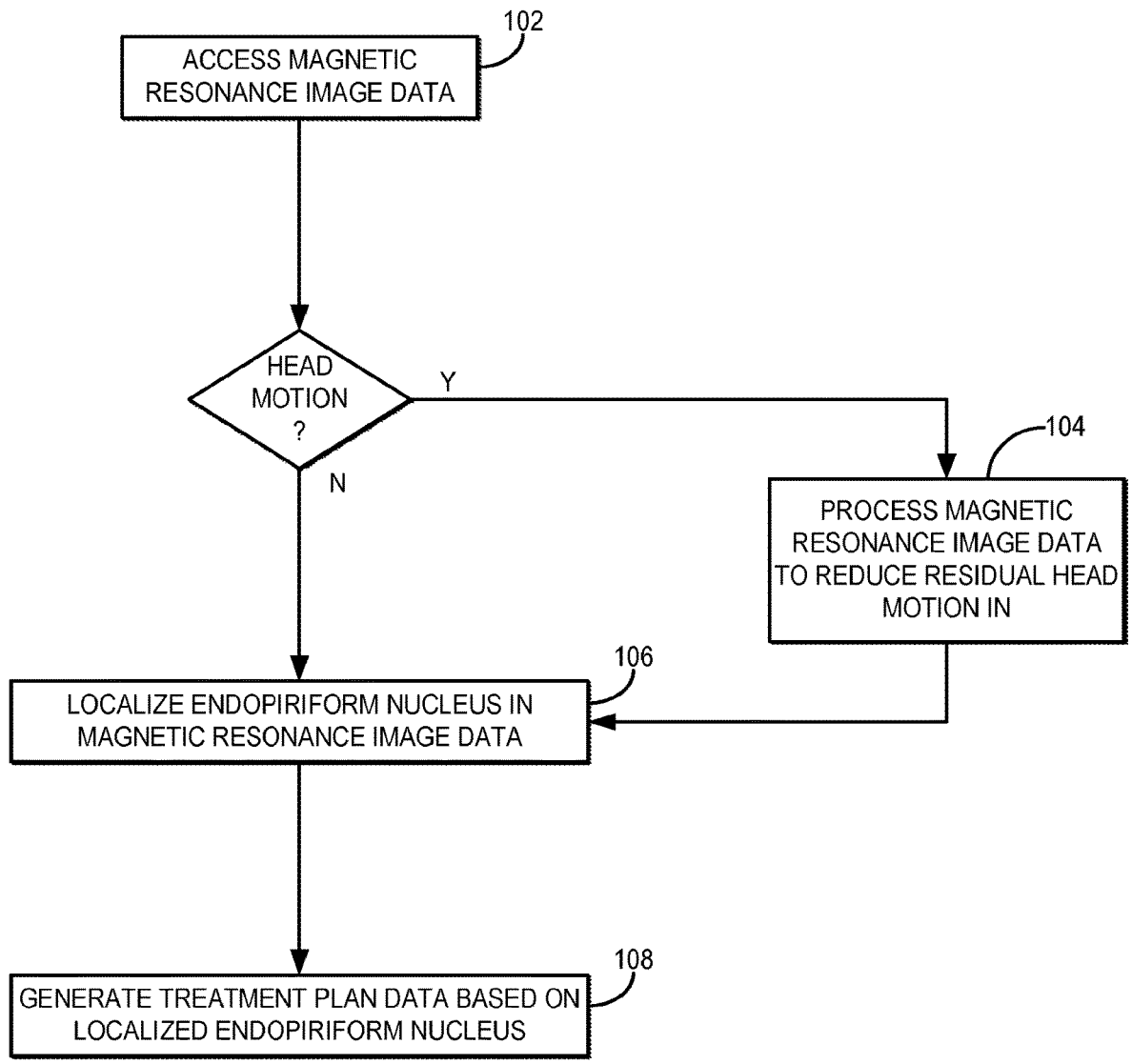
FIG. 1 is a flowchart setting forth the steps of an example method for generating treatment plan data for delivering neuromodulation treatment to the endopiriform nucleus of a subject based on magnetic resonance image data acquired from the subject.

Described here are systems and methods for magnetic resonance imaging ("MRI") based localization of endopiriform nucleus ("EPN") as a target for neuromodulation treatment, such as for neuromodulation treatment of epilepsy, other neurological disorders (e.g., other neurological brain circuit disorders), or other neurological conditions, which may include conditions affecting attention (e.g., attention deficit disorder), conditions affecting memory (e.g., dysfunction with immediate recall, delayed recall, dementia), and conditions affecting the olfactory system.

There is a large unmet patient need for reliable neuromodulation to treat epilepsy and other neurological disorders or conditions. It is an aspect of the present disclosure that the EPN, which is located in the deep mesial frontal lobe-temporal lobe junctional regions bilaterally, plays a significant role in regulating cortical hypersynchronous excitability and the propagation of seizure activity in epilepsy. Thus, as one non-limiting example, neuromodulation therapy can be used to target and modulate the EPN in the treatment of epilepsy or other neurological brain circuit disorders.

Neuromodulation can be provided using deep brain stimulation ("DBS"); electrodes, including segmented electrodes, directional electrodes, multiple independent current control, or other custom electrode designs based on patient-specific EPN location or geometry; or closed-loop recording and stimulation. In these examples, electrical stimulation can be provided using low-frequency paradigms, high-frequency paradigms, or both. Additionally or alternatively, electrical stimulation can be provided using unilateral biphasic electrical stimulation, bilateral biphasic electrical stimulation, or a combination of both.

In still other implementations, neuromodulation can be provided using local delivery of medication; focused ultrasound; transcranial magnetic stimulation; resection therapy, including open resection, stereotactic resection, or endoscopic minimally invasive resection; ablation, including radiosurgery (e.g., via CyberKnife®, Gamma Knife®), focused ultrasound, radio frequency ("RF"), or laser interstitial thermal therapy ("LITT") ablation; or other suitable therapies for implementing neuromodulation, including optogenetics, stem cell implantation, and local delivery of medication and other chemical substances.

In order to localize or otherwise visualize the EPN in subjects, the systems and methods described in the present disclosure provide MRI techniques that are capable of measuring stereotactic coordinates, or other coordinate data or trajectory data, that can then be used to target interventions into the EPN. When the EPN has been localized, neuromodulation or other treatment can be delivered to the EPN. It is another aspect of the present disclosure to provide neurosurgical techniques in which a trajectory for safe stereotactic targeting of EPNs, bilaterally, can be mapped based on images obtained with MRI.

As noted above, because the EPN plays a role in regulating cortical hypersynchronous excitability and in the propagation of seizures, it is a suitable target, either unilaterally or bilaterally, for therapies. However, given its size, anatomical location, and contrast relative to surrounding anatomical structures, the EPN is a challenging structure to image with MRI. For instance, it can generally be challenging to isolate the EPN from its adjacent structures, such as the adjacent piriform cortex, amygdala, claustrum, and ventral putamen. As such, the EPN is not considered to be a structure that neuroradiologists can routinely localize, even using state-of-the-art clinical brain MRI data sets. Additionally, delivering neuromodulation treatment to the EPN can be challenging because of the EPN's location relative to the nearby cerebral artery.

Because of these considerations, it is important that the EPN be accurately localized in order to safely deliver neuromodulation therapy. To delivery or otherwise execute therapies delivered to the EPN (e.g., neuromodulation therapies), the systems and methods described in the present disclosure provide subject-specific MRI-based targeting for surgical and stereotactic approaches.

In some implementations, targeting of the EPN can be augmented with other imaging modalities. For instance, EPN can be targeted after visualization with MRI along with other imaging modalities to identify the known landmarks and adjacent structures. These other imaging modalities may include x-ray imaging, including fluoroscopy, ventriculography, and computed tomography ("CT"); ultrasound; or other suitable medical imaging modalities.

Treatment plan data can include stereotactic coordinate data, which may include coordinate data in a stereotactic atlas and anterior commissure-posterior commissure, or other suitable, coordinate system. Treatment plan data can also include other coordinate data for use with neurosurgical guidance systems, surgical navigation systems, and so on. In some instances, the treatment plan data may also include trajectory data, such as data depicting, or otherwise representing or indicating, a planned trajectory for treating the EPN with a particular neuromodulation therapy. The treatment plan data may be of a form and structure capable of being input to stereotactic targeting software or systems, or in conjunction with instruments such as stereotactic frame systems. The treatment plan data can also be in a form and structure capable of being input to surgical robots.

Referring now to FIG. 1, a flowchart is illustrated as setting forth the steps of an example method for targeting or otherwise localizing a subject's endopiriform nucleus ("EPN") based on images or other data obtained with an MRI system.

The method includes accessing, with a computer system, magnetic resonance image data obtained from the subject with an MRI system, as indicated at step 102. The magnetic resonance image data can be accessed by retrieving previously acquired data from a memory or other suitable data storage device or medium. Additionally or alternatively, the data can be accessed by acquiring the data using an MRI system and communicating or otherwise transferring the data to the computer system, which may form a part of the MRI system. The magnetic resonance image data may be two-dimensional data (e.g., images obtained from multiple different slices), three-dimensional data (e.g., volumetric images obtained from one or more imaging volumes), or both.

In general, the magnetic resonance image data contains images acquired using an ultra-high field ("UHF") MRI system. For instance, UHF MRI systems have magnetic field strengths greater than 3 T. As one non-limiting example, UHF MRI systems have a magnetic field strength of at least 7 T. These UHF MRI systems achieve higher signal-to-noise ratio ("SNR") and higher intrinsic tissue contrast obtained as compared with lower field strength of clinical scanners operating at 1.5 T or 3 T, which have lower spatial and contrast resolution. As an example, brain imaging at 7 T using the systems and methods described in the present disclosure is capable of achieving very high spatial resolution (e.g., 0.25 mm×0.25 mm in plane, with a slice thickness that does not exceed 1.2 mm).

The magnetic resonance image data can include images obtained with T2-weighting, which has been found to be advantageous for imaging the anatomical extent and boundaries of the EPN. As one non-limiting example, T2-weighted images may be obtained using a T2-weighted turbo spin echo ("TSE") pulse sequence. Additionally or alternatively, the magnetic resonance image data can also include images obtained with different tissue contrasts, such as T1-weighting, proton density weighting, or both. For instance, T1-weighted and/or proton density-weighted images can provide complementary information that is advantageous for prescribing the position for a T2-weighted acquisition, as well as to provide brain volumetry and to cross-match structural boundaries as seen in T2-weighted images with those as seen in T1-weighted images. As another non-limiting example, T1-weighted images can be obtained using a T1-weighted magnetization prepared rapid gradient echo ("MPRAGE") pulse sequence. The magnetic resonance image data can also include images acquired with additional contrast weightings, such as susceptibility weighting, diffusion weighting, perfusion weighting, and so on. Thus, in some instances the magnetic resonance image data may also include quantitative susceptibility maps, diffusion-based fiber tracking maps, perfusion maps, and so on. Additionally or alternatively, the magnetic resonance image data may include localized magnetic resonance spectroscopy data.

As a non-limiting example, T1-weighted images and T2-weighted images may be obtained using an imaging protocol that includes scout images for positioning; Bo shimming; whole-brain 3D T1-weighted MPRAGE (resolution of, for example, 0.8×0.8×0.8 mm³ or 0.67×0.67×0.67 mm³); whole-brain 3D GRE at the same resolution as the T1-weighted MPRAGE (e.g., same sequence without inversion RF pulse), which is dominated by proton density contrast; and T2-weighted TSE 2D acquisitions. Once acquired, the T1-weighted dataset can be utilized to graphically position a stack of multi-slice high resolution T2-weighted TSE images (e.g., with resolution of 0.25× 0.25×1.2 mm³), which may in some instances be obtained in a coronal oblique orientation, perpendicular to the average long axis of the bodies of the right and left hippocampus. In some instances, these T2-weighted TSE data may be acquired with an interleaved multi-slab scheme.

In some implementations, the magnetic resonance images are acquired using a multislice acquisition, in which data are acquired using an interleaved acquisition subset between odd and even distributed slices. This interleaved acquisition strategy can be useful for avoiding interactions between adjacent slices, such as interactions related to residual head motion during the acquisition of each interleaved stack of slices. As such, a multislice acquisition with interleaved odd and even slices can reduce residual head motion, which if left unaddressed can result in lower image quality, especially at the high spatial resolutions attainable with UHF MRI systems.

Additionally or alternatively, the images may be processed to reduce or otherwise remove residual head motion or errors related to residual head motion, as indicated at optional step 104. For instance, in some instances, high resolution (e.g., 0.25×25 mm²) multislice T2-weighted TSE data with 1.2 mm slice thickness may be prone to frequent motion artifacts when collected in contiguous slices (even in interleaved slice order), or when an individual scan exceeds a certain duration of time, such as about 5 minutes. In these instances, a full stack of 2D high resolution data can be collected in several subsets. For instance, a full stack can be split into a number of slabs ($N_{slab}$, with values such as $N_{slab}$=2, 3, 4, . . . , depending on the total extent of brain tissue to be covered). For each slab odd and even numbered slices can be collected in two separate sub-slab scans. Combining these ($N_{slab}$×2) data sets can result in higher quality images with significantly reduced occurrence of motion artifacts. In order to spatially co-register the (e.g., $N_{slab}$×2) individual subsets, one additional multislice T2-weighted TSE image can be obtained with half the spatial resolution along the phase-encoding axis (0.25×0.5× 1.2 mm³). The lower resolution of the latter considerably reduces its sensitivity to motion artifacts, which supports co-registration of the entire T2-weighted stack to this reference point. Other motion correction techniques may also be employed, including using retrospective motion correction techniques.

The magnetic resonance image data are then analyzed with the computer system in order to identify or otherwise localize the EPN, as indicated at step 106. The One or both of the left EPN and right EPN can be identified or otherwise localized. In some instances, the EPN can be identified or otherwise localized by segmenting T2-weighted images contained in the magnetic resonance image data. For example, the EPN can be identified or otherwise localized by segmenting the T2-weighted images using a manual segmentations (e.g., segmentation performed by a user), or an automated or semi-automated segmentation. As another example, the EPN can be identified or otherwise localized by localizing the center or some other portion of the EPN based on a relative location from adjacent landmarks (e.g., anatomical landmarks) outside of the EPN, which may be identified in the magnetic resonance image data. As still another example, the EPN can be identified or otherwise localized based in part on a comparison with standard anatomical atlas data. These anatomical atlas data may be derived from cadaver brains, or from medical imaging (e.g., MRI) of in vivo or ex vivo brains. In this way, the anatomical atlas data can be used to determine stereotactic coordinate data of the expected EPN location within the subject.

In an example implementation, and with reference to the imaging protocol described above, segmentation can be performed using FreeSurfer (http://surfer.nmr.mgh.harvard-.edu/) to segment the bilateral cerebral hemispheric volume in the T1w-GRE ratio image set. Before launching the full brain segmentation, the mask obtained after skull stripping can be visually inspected. Automatic brain segmentation can be completed with FreeSurfer. The resulting segmentation and T1w-GRE ratio images can then be exported into 3D Slicer, where 3D editing tools can be used to adjust individual segmentation boundaries as needed. For example, the medial border of the diencephalon segments can be adjusted to exclude clustered blood vessels of the third ventricle from the gray matter segment. Total bihemispheric gray and white matter volumes can be calculated by summing the volumes of the supratentorial brain segments, excluding the ventricles and other CSF spaces, optic chiasm, brainstem, and cerebellum.

In some instances, the magnetic resonance image data can include additional images other than T2-weighted images, as described above. As one non-limiting example, the EPN can be identified or otherwise localized by segmenting T2-weighted images in such a way that the segmentation is guided by information or data in the other images. For instance, fiber tracking maps can be used to identify or otherwise localize thin white matter bundles that may otherwise confound the localization of the EPN. Using data from the fiber tracking maps, these thin white matter bundles can be separated from adjacent structures, thereby improving the localization accuracy of identifying the EPN. Similarly, other images can be used to provide complementary information about the location and anatomical extent of the EPN, including T1-weighted and proton-weighted images. In still other embodiments, the computer system can access other medical image data obtained with a different imaging modality to further assist the localization of the EPN, including those imaging modalities noted above.

As a non-limiting example, using the imaging protocol described above, T1-weighted MPRAGE and GRE 3D data sets can be co-registered to address inter-scan motion. Then, in order to eliminate large field bias observed at 7 T (dominated by the RF coil receive sensitivity), the T1-weighted volume can be divided by the GRE volume after adding a constant offset (e.g., an empirically determined constant offset) to the GRE images to avoid excessive brightness when dividing by background noise values close to zero. The resulting ratio image, which is devoid of $T_2^*$, proton density, and receive $B_1$ signal variations can then be utilized to perform automatic brain segmentation.

As another non-limiting example, and again using the imaging protocol described above, because of the non-contiguous multi-2D slice acquisition of the high resolution T2-weighted images, high-resolution T2-weighted sub-slabs can be co-registered onto a stack of contiguous lower resolution T2-weighted slices. Briefly, the low resolution contiguous volume can be interpolated to the same pixel size as the high resolution sub-slabs. Each high resolution sub-slab can be embedded in a full volume matrix where non-imaged pixels are set to zero (i.e., gaps between imaged slices). Each such volume can be coregistered to the low resolution volume, such as by using a rigid transformation based on normalized mutual information criterion and B-spline interpolation, or using other suitable techniques. The transformation matrix computed for each high-resolution sub-slab can then be applied to the corresponding binary volume mask as well. The final high-resolution volume can be obtained by dividing the sum of the registered high-resolution volumes by the sum of the registered masks in order to avoid signal intensity mismatch that may result from partial overlap between adjacent slices. These co-registered high-resolution T2-weighted volumes can then be utilized for identifying and segmenting the EPNs.

Based on the identified or otherwise localized EPN in the magnetic resonance image data, treatment plan data can be generated for guiding treatment to the EPN, as indicated at step 108. The treatment plan data may include, for instance, coordinate data that define or otherwise describe the location and anatomical extent of the EPN in a particular coordinate system. The coordinate data may indicate coordinates in an anatomical coordinate system, a stereotactic coordinate system, or other suitable coordinate system associated with a surgical navigation system, surgical guidance system, or other treatment navigation or guidance system. As one non-limiting example, the coordinate data can be stereotactic coordinate data that define or otherwise describe the location, anatomical extent, or both, of the EPN in a stereotactic coordinate system.

Additionally or alternatively, the treatment plan data can include trajectory data that define or otherwise describe a trajectory for directing neuromodulation to the identified EPN location. For instance, trajectory data may include one or more trajectories for guiding a surgical intervention or medical instrument (e.g., electrodes, ablation catheters) to the identified EPN location. The trajectory data may include one or more trajectories that are optimized to avoid critical structures, such as cerebral vasculature adjacent the EPN and along the trajectory. In still other examples, the trajectory data can include one or more trajectories for delivering radiation, focused ultrasound, or other energy to the identified EPN location. Such trajectories can be optimized to minimize interaction with adjacent critical or sensitive structures.

As one non-limiting example, the general location of the EPN is amenable to a frontal approach/trajectory that is traditional for external ventricular drains or DBS. Typically, the cortical access would be near/in front of the Kocher's point, in front of the coronal suture, and approximately 3 cm lateral to the midline. Stereotactic navigation can be used to select a safe trajectory, avoiding major vasculature. The patient-specific localization of the EPN using the systems and methods described in the present disclosure enable a safe trajectory to be determined based on these considerations.

As another non-limiting example, the general location of the EPN is also amenable to a lateral approach/trajectory, with cortical access being in the temporal lobe and the trajectory being approximately orthogonal to the skull to reach the target. Stereotactic navigation can again be used to select a safe trajectory, avoiding major vasculature. The patient-specific localization of the EPN using the systems and methods described in the present disclosure enable a safe trajectory to be determined based on these considerations.

As still another non-limiting example, the general location of the EPN is also amenable to an occipital approach/trajectory, with the cortical access in the occipital lobe and directed frontally. In these instances, trajectory often takes a mesial direction approaching the EPN. Stereotactic navigation can again be used to select a safe trajectory, avoiding major vasculature. The patient-specific localization of the EPN using the systems and methods described in the present disclosure enable a safe trajectory to be determined based on these considerations.

Additionally or alternatively, the treatment plan data can be generated to include both data localizing the EPN and data localizing one or more target regions in the hippocampus or other locations in the subject's brain, spinal cord, central nervous system, peripheral nervous system, or other organ systems or anatomical locations. The magnetic resonance image data can therefore be further analyzed to identify or otherwise localize the hippocampus or other target region in the subject. These additional data are then used to target the hippocampus or other target region. In these implementations, the treatment plan data can be used to direct neuromodulation treatment to the EPN while recording or otherwise measuring data (e.g., electrical or other measurements of neuronal activity) in the one or more target regions in the hippocampus. Similarly, data may be measured at the EPN while neuromodulation is directed to the hippocampus or other target region. Advantageously, the measurements from the hippocampus can be used to monitor and adapt the neuromodulation delivered to the EPN. For example, the measurement data from the hippocampus can be used as an input to a closed-loop feedback system for adapting the parameters of the neuromodulation being delivered to the EPN. The parameters may include operational parameters for the system used to deliver the neuromodulation, which may include a DBS or other electrode-based system, a focused ultrasound system, an RF ablation system, a laser ablation system, and so on. In some implementations, the neuromodulation can include pharmaceutical therapies or behavioral therapies. In these instances, the parameters of the various therapies (e.g., dose of medication, selection of medication, method of delivering a medication) can be similarly adjusted based on feedback from data measured at the EPN or other target region.

In some embodiments, the treatment plan data may include one or more display elements that may be generated on a graphical user interface ("GUI") for visualization by a user. For instance, the treatment plan data may include one or more display elements that represent the location, spatial extent, or both, of the localized EPN. These one or more display elements may also include textual or numerical data representative of coordinate data corresponding to the localized EPN.

As another example, the one or more display elements may represent one or more trajectories for delivering treatment (e.g., neuromodulation treatment) to the localized EPN. For instance, these display elements can include linear display elements that represent the trajectories for delivering treatment to the EPN. In some embodiments, the GUI can allow for user interaction with the displayed trajectories. For example, the GUI can be programmed or otherwise configured to enable a user to move, reorient, or otherwise adjust the displayed trajectories. In this way, the GUI can provide for manual adjustment of the planned trajectory, or trajectories, for delivering treatment to the EPN.

The display elements can be generated and displayed in conjunction with the magnetic resonance image data. For instance, the display elements can be overlaid on images contained in the magnetic resonance image data. This enables the user to visualize the localized EPN and other treatment plan data (e.g., coordinate data, trajectory data) relative to the imaged patient anatomy.

The systems and methods described in the present disclosure provide for improved EPN target and therapy efficacy. In addition to enabling more accurate EPN localization and treatment planning, the systems and methods described in the present disclosure can also provide for designing optimized or otherwise patient-specific electrodes. For instance, based on the localized EPN, patient-specific electrode lead designs can be generated such that electrical stimulation treatment is optimized for delivery to that particular patient's EPN.

Figure 2:
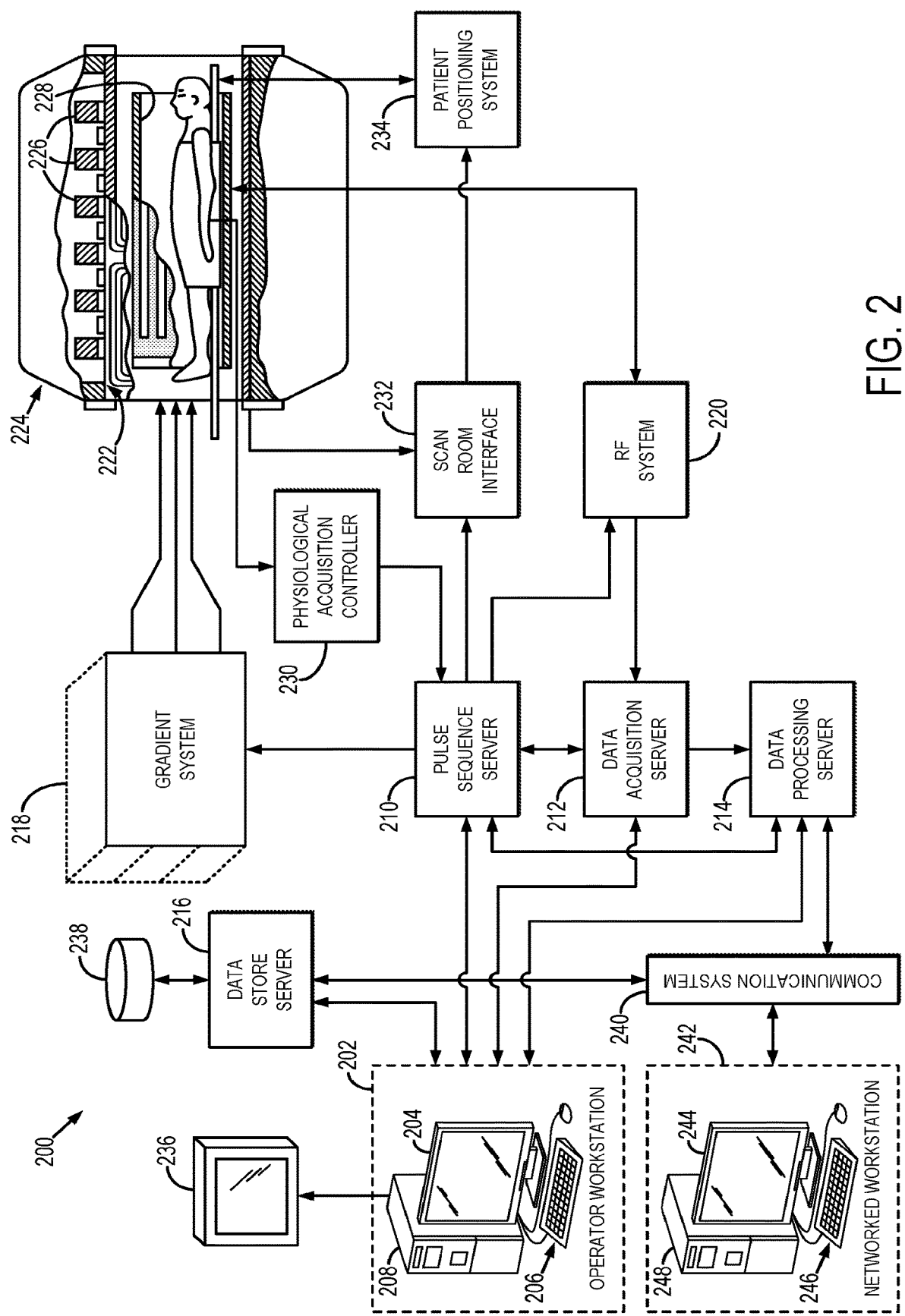
FIG. 2 is a block diagram of an example magnetic resonance imaging ("MRI") system that can implement the methods described in the present disclosure.

Referring particularly now to FIG. 2, an example of an MRI system 200 that can implement the methods described here is illustrated. The MRI system 200 includes an operator workstation 202 that may include a display 204, one or more input devices 206 (e.g., a keyboard, a mouse), and a processor 208. The processor 208 may include a commercially available programmable machine running a commercially available operating system. The operator workstation 202 provides an operator interface that facilitates entering scan parameters into the MRI system 200. The operator workstation 202 may be coupled to different servers, including, for example, a pulse sequence server 210, a data acquisition server 212, a data processing server 214, and a data store server 216. The operator workstation 202 and the servers 210, 212, 214, and 216 may be connected via a communication system 240, which may include wired or wireless network connections.

The pulse sequence server 210 functions in response to instructions provided by the operator workstation 202 to operate a gradient system 218 and a radiofrequency ("RF") system 220. Gradient waveforms for performing a prescribed scan are produced and applied to the gradient system 218, which then excites gradient coils in an assembly 222 to produce the magnetic field gradients $G_x$, $G_y$, and $G_z$ that are used for spatially encoding magnetic resonance signals. The gradient coil assembly 222 forms part of a magnet assembly 224 that includes a polarizing magnet 226 and a whole-body RF coil 228.

In some configurations, the polarizing magnet 226 generates a magnetic field with an ultra-high field strength. For instance, the magnetic field can have a field strength that is greater than 3 T. As one example, the magnetic field can have a field strength of at least 7 T.

RF waveforms are applied by the RF system 220 to the RF coil 228, or a separate local coil to perform the prescribed magnetic resonance pulse sequence. Responsive magnetic resonance signals detected by the RF coil 228, or a separate local coil, are received by the RF system 220. The responsive magnetic resonance signals may be amplified, demodulated, filtered, and digitized under direction of commands produced by the pulse sequence server 210. The RF system 220 includes an RF transmitter for producing a wide variety of RF pulses used in MRI pulse sequences. The RF transmitter is responsive to the prescribed scan and direction from the pulse sequence server 210 to produce RF pulses of the desired frequency, phase, and pulse amplitude waveform. The generated RF pulses may be applied to the whole-body RF coil 228 or to one or more local coils or coil arrays.

The RF system 220 also includes one or more RF receiver channels. An RF receiver channel includes an RF preamplifier that amplifies the magnetic resonance signal received by the coil 228 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (1);$$

and the phase of the received magnetic resonance signal may also be determined according to the following relationship:

$$\varphi = \tan^{-1}\left(\frac{Q}{I}\right). \qquad (2)$$

The pulse sequence server 210 may receive patient data from a physiological acquisition controller 230. By way of example, the physiological acquisition controller 230 may receive signals from a number of different sensors connected to the patient, including electrocardiograph ("ECG") signals from electrodes, or respiratory signals from a respiratory bellows or other respiratory monitoring devices. These signals may be used by the pulse sequence server 210 to synchronize, or "gate," the performance of the scan with the subject's heart beat or respiration.

The pulse sequence server 210 may also connect to a scan room interface circuit 232 that receives signals from various sensors associated with the condition of the patient and the magnet system. Through the scan room interface circuit 232, a patient positioning system 234 can receive commands to move the patient to desired positions during the scan.

The digitized magnetic resonance signal samples produced by the RF system 220 are received by the data acquisition server 212. The data acquisition server 212 operates in response to instructions downloaded from the operator workstation 202 to receive the real-time magnetic resonance data and provide buffer storage, so that data is not lost by data overrun. In some scans, the data acquisition server 212 passes the acquired magnetic resonance data to the data processor server 214. In scans that require information derived from acquired magnetic resonance data to control the further performance of the scan, the data acquisition server 212 may be programmed to produce such information and convey it to the pulse sequence server 210. For example, during pre-scans, magnetic resonance data may be acquired and used to calibrate the pulse sequence performed by the pulse sequence server 210. As another example, navigator signals may be acquired and used to adjust the operating parameters of the RF system 220 or the gradient system 218, or to control the view order in which k-space is sampled. In still another example, the data acquisition server 212 may also process magnetic resonance signals used to detect the arrival of a contrast agent in a magnetic resonance angiography ("MRA") scan. For example, the data acquisition server 212 may acquire magnetic resonance data and processes it in real-time to produce information that is used to control the scan.

The data processing server 214 receives magnetic resonance data from the data acquisition server 212 and processes the magnetic resonance data in accordance with instructions provided by the operator workstation 202. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 214 are conveyed back to the operator workstation 202 for storage. Real-time images may be stored in a data base memory cache, from which they may be output to operator display 202 or a display 236. Batch mode images or selected real time images may be stored in a host database on disc storage 238. When such images have been reconstructed and transferred to storage, the data processing server 214 may notify the data store server 216 on the operator workstation 202. The operator workstation 202 may be used by an operator to archive the images, produce films, or send the images via a network to other facilities.

The MRI system 200 may also include one or more networked workstations 242. For example, a networked workstation 242 may include a display 244, one or more input devices 246 (e.g., a keyboard, a mouse), and a processor 248. The networked workstation 242 may be located within the same facility as the operator workstation 202, or in a different facility, such as a different healthcare institution or clinic.

The networked workstation 242 may gain remote access to the data processing server 214 or data store server 216 via the communication system 240. Accordingly, multiple networked workstations 242 may have access to the data processing server 214 and the data store server 216. In this manner, magnetic resonance data, reconstructed images, or other data may be exchanged between the data processing server 214 or the data store server 216 and the networked workstations 242, such that the data or images may be remotely processed by a networked workstation 242.

Figure 3:
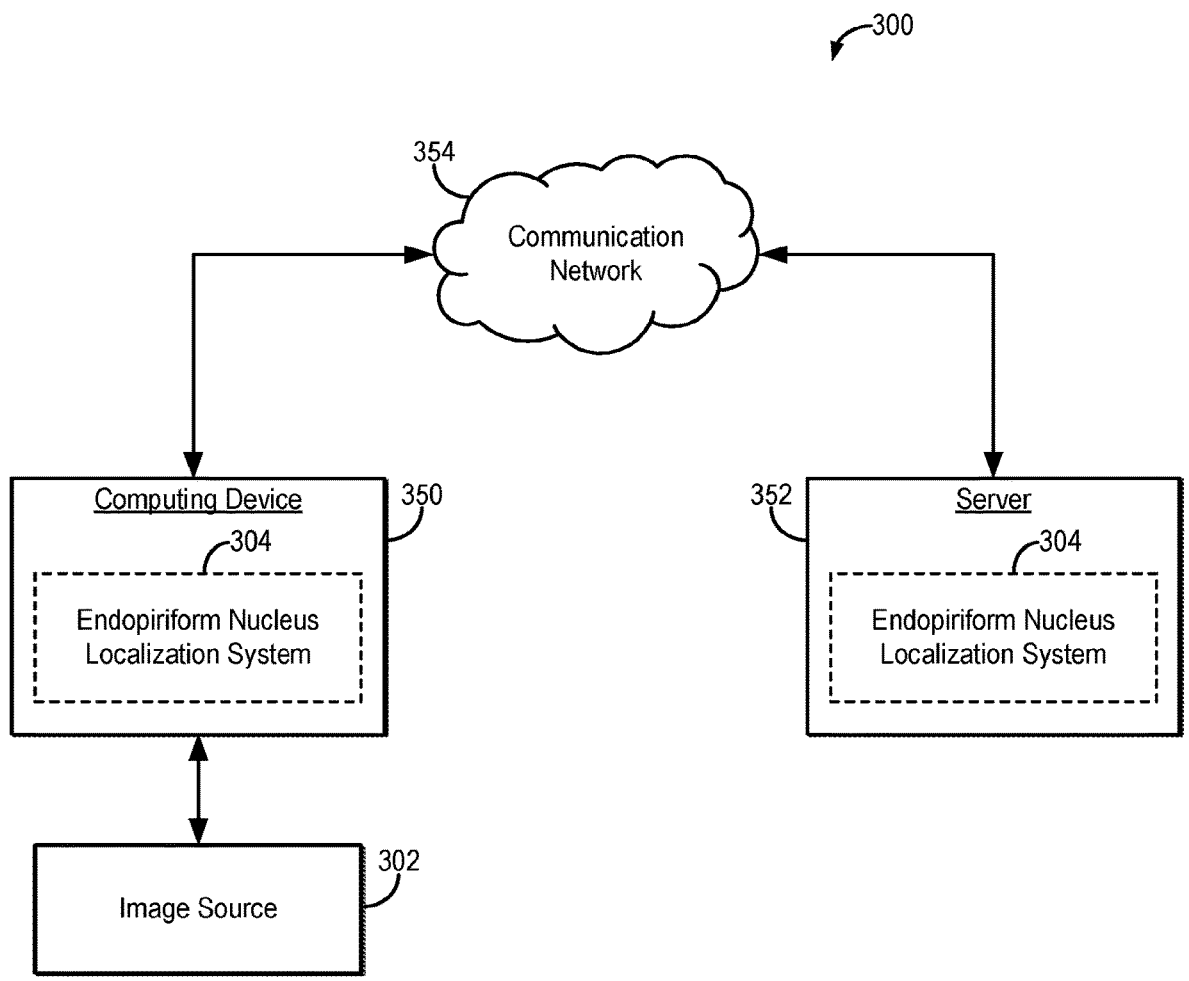
FIG. 3 is a block diagram of an example endopiriform nuclear localization system that can implement methods described in the present disclosure.

Referring now to FIG. 3, an example of a system 300 for localizing EPN based on MRI in accordance with some embodiments of the systems and methods described in the present disclosure is shown. As shown in FIG. 3, a computing device 350 can receive one or more types of data (e.g., k-space data, magnetic resonance images) from image source 302, which may be an MRI image source. In some embodiments, computing device 350 can execute at least a portion of an EPN localization system 304 to localize EPN and generate treatment plan data from data received from the image source 302. The treatment plan data may include, for example, stereotactic coordinate data or other treatment trajectory data for directing neuromodulation treatment to the localized EPN in a subject-specific manner.

Additionally or alternatively, in some embodiments, the computing device 350 can communicate information about data received from the image source 302 to a server 352 over a communication network 354, which can execute at least a portion of the EPN localization system 304. In such embodiments, the server 352 can return information to the computing device 350 (and/or any other suitable computing device) indicative of an output of the EPN localization system 304.

In some embodiments, computing device 350 and/or server 352 can be any suitable computing device or combination of devices, such as a desktop computer, a laptop computer, a smartphone, a tablet computer, a wearable computer, a server computer, a virtual machine being executed by a physical computing device, and so on. The computing device 350 and/or server 352 can also reconstruct images from the data.

In some embodiments, image source 302 can be any suitable source of image data (e.g., measurement data, images reconstructed from measurement data), such as an MRI system, another computing device (e.g., a server storing image data), and so on. In some embodiments, image source 302 can be local to computing device 350. For example, image source 302 can be incorporated with computing device 350 (e.g., computing device 350 can be configured as part of a device for capturing, scanning, and/or storing images). As another example, image source 302 can be connected to computing device 350 by a cable, a direct wireless link, and so on. Additionally or alternatively, in some embodiments, image source 302 can be located locally and/or remotely from computing device 350, and can communicate data to computing device 350 (and/or server 352) via a communication network (e.g., communication network 354).

In some embodiments, communication network 354 can be any suitable communication network or combination of communication networks. For example, communication network 354 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 3 can each be any suitable communications link or combination of communications links, such as wired links, fiber optic links, Wi-Fi links, Bluetooth links, cellular links, and so on.

Figure 4:
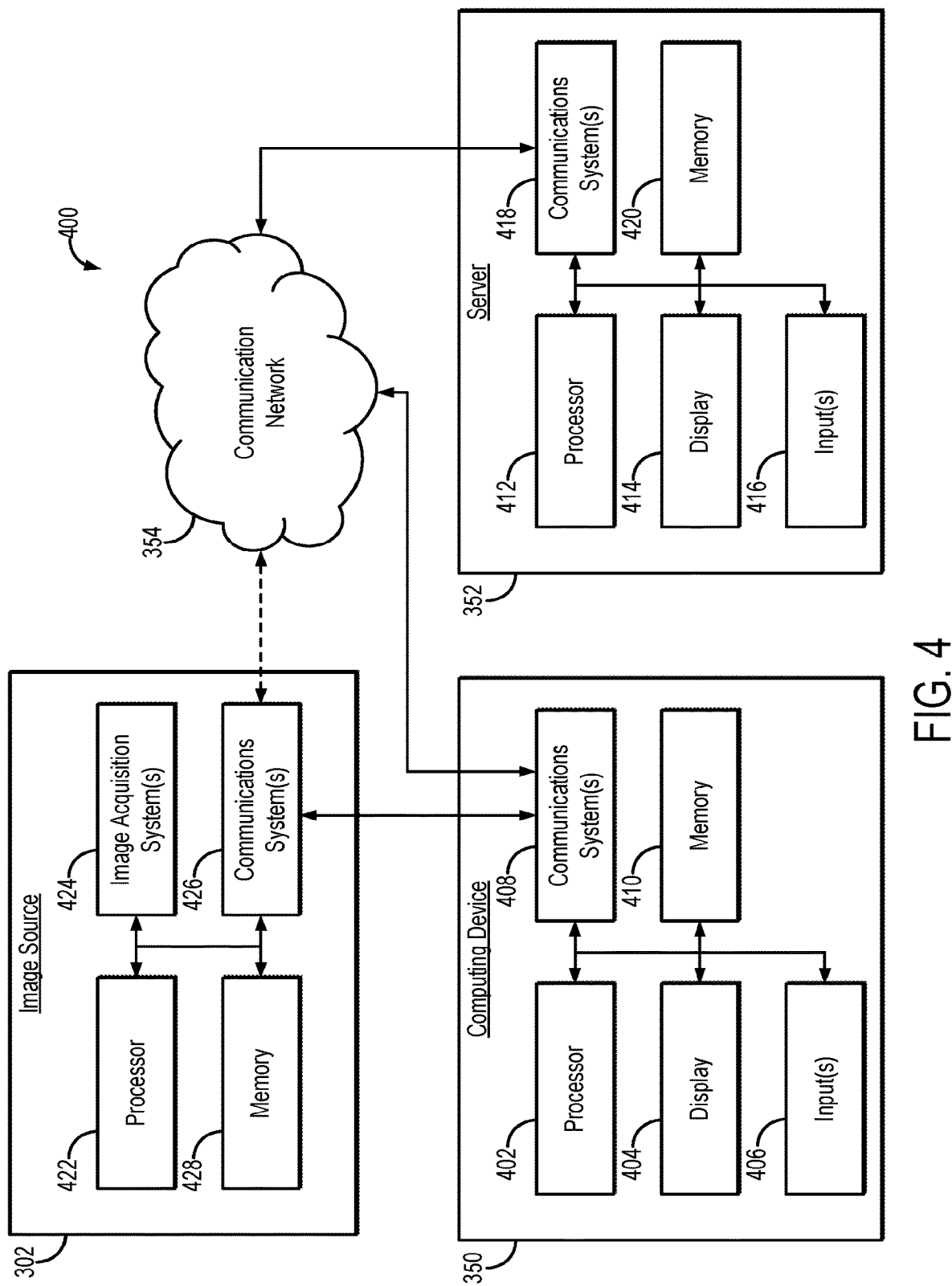
FIG. 4 is a block diagram of example components of the endopiriform nucleus localization system of FIG. 3.

Referring now to FIG. 4, an example of hardware 400 that can be used to implement image source 302, computing device 350, and server 354 in accordance with some embodiments of the systems and methods described in the present disclosure is shown. As shown in FIG. 4, in some embodiments, computing device 350 can include a processor 402, a display 404, one or more inputs 406, one or more communication systems 408, and/or memory 410. In some embodiments, processor 402 can be any suitable hardware processor or combination of processors, such as a central processing unit ("CPU"), a graphics processing unit ("GPU"), and so on. In some embodiments, display 404 can include any suitable display devices, such as a computer monitor, a touchscreen, a television, and so on. In some embodiments, inputs 406 can include any suitable input devices and/or sensors that can be used to receive user input, such as a keyboard, a mouse, a touchscreen, a microphone, and so on.

In some embodiments, communications systems 408 can include any suitable hardware, firmware, and/or software for communicating information over communication network 354 and/or any other suitable communication networks. For example, communications systems 408 can include one or more transceivers, one or more communication chips and/or chip sets, and so on. In a more particular example, communications systems 408 can include hardware, firmware and/or software that can be used to establish a Wi-Fi connection, a Bluetooth connection, a cellular connection, an Ethernet connection, and so on.

In some embodiments, memory 410 can include any suitable storage device or devices that can be used to store instructions, values, data, or the like, that can be used, for example, by processor 402 to present content using display 404, to communicate with server 352 via communications system(s) 408, and so on. Memory 410 can include any suitable volatile memory, non-volatile memory, storage, or any suitable combination thereof. For example, memory 410 can include RAM, ROM, EEPROM, one or more flash drives, one or more hard disks, one or more solid state drives, one or more optical drives, and so on. In some embodiments, memory 410 can have encoded thereon, or otherwise stored therein, a computer program for controlling operation of computing device 350. In such embodiments, processor 402 can execute at least a portion of the computer program to present content (e.g., images, user interfaces, graphics, tables), receive content from server 352, transmit information to server 352, and so on.

In some embodiments, server 352 can include a processor 412, a display 414, one or more inputs 416, one or more communications systems 418, and/or memory 420. In some embodiments, processor 412 can be any suitable hardware processor or combination of processors, such as a CPU, a GPU, and so on. In some embodiments, display 414 can include any suitable display devices, such as a computer monitor, a touchscreen, a television, and so on. In some embodiments, inputs 416 can include any suitable input devices and/or sensors that can be used to receive user input, such as a keyboard, a mouse, a touchscreen, a microphone, and so on.

In some embodiments, communications systems 418 can include any suitable hardware, firmware, and/or software for communicating information over communication network 354 and/or any other suitable communication networks. For example, communications systems 418 can include one or more transceivers, one or more communication chips and/or chip sets, and so on. In a more particular example, communications systems 418 can include hardware, firmware and/or software that can be used to establish a Wi-Fi connection, a Bluetooth connection, a cellular connection, an Ethernet connection, and so on.

In some embodiments, memory 420 can include any suitable storage device or devices that can be used to store instructions, values, data, or the like, that can be used, for example, by processor 412 to present content using display 414, to communicate with one or more computing devices 350, and so on. Memory 420 can include any suitable volatile memory, non-volatile memory, storage, or any suitable combination thereof. For example, memory 420 can include RAM, ROM, EEPROM, one or more flash drives, one or more hard disks, one or more solid state drives, one or more optical drives, and so on. In some embodiments, memory 420 can have encoded thereon a server program for controlling operation of server 352. In such embodiments, processor 412 can execute at least a portion of the server program to transmit information and/or content (e.g., data, images, a user interface) to one or more computing devices 350, receive information and/or content from one or more computing devices 350, receive instructions from one or more devices (e.g., a personal computer, a laptop computer, a tablet computer, a smartphone), and so on.

In some embodiments, image source 302 can include a processor 422, one or more image acquisition systems 424, one or more communications systems 426, and/or memory 428. In some embodiments, processor 422 can be any suitable hardware processor or combination of processors, such as a CPU, a GPU, and so on. In some embodiments, the one or more image acquisition systems 424 are generally configured to acquire data, images, or both, and can include an MRI system. Additionally or alternatively, in some embodiments, one or more image acquisition systems 424 can include any suitable hardware, firmware, and/or software for coupling to and/or controlling operations of an MRI system. In some embodiments, one or more portions of the one or more image acquisition systems 424 can be removable and/or replaceable.

Note that, although not shown, image source 302 can include any suitable inputs and/or outputs. For example, image source 302 can include input devices and/or sensors that can be used to receive user input, such as a keyboard, a mouse, a touchscreen, a microphone, a trackpad, a trackball, and so on. As another example, image source 302 can include any suitable display devices, such as a computer monitor, a touchscreen, a television, etc., one or more speakers, and so on.

In some embodiments, communications systems 426 can include any suitable hardware, firmware, and/or software for communicating information to computing device 350 (and, in some embodiments, over communication network 354 and/or any other suitable communication networks). For example, communications systems 426 can include one or more transceivers, one or more communication chips and/or chip sets, and so on. In a more particular example, communications systems 426 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 428 can include any suitable storage device or devices that can be used to store instructions, values, data, or the like, that can be used, for example, by processor 422 to control the one or more image acquisition systems 424, and/or receive data from the one or more image acquisition systems 424; to images from data; present content (e.g., images, a user interface) using a display; communicate with one or more computing devices 350; and so on. Memory 428 can include any suitable volatile memory, non-volatile memory, storage, or any suitable combination thereof. For example, memory 428 can include RAM, ROM, EEPROM, one or more flash drives, one or more hard disks, one or more solid state drives, one or more optical drives, and so on. In some embodiments, memory 428 can have encoded thereon, or otherwise stored therein, a program for controlling operation of image source 302. In such embodiments, processor 422 can execute at least a portion of the program to generate images, transmit information and/or content (e.g., data, images) to one or more computing devices 350, receive information and/or content from one or more computing devices 350, receive instructions from one or more devices (e.g., a personal computer, a laptop computer, a tablet computer, a smartphone, etc.), and so on.

Figure 5:
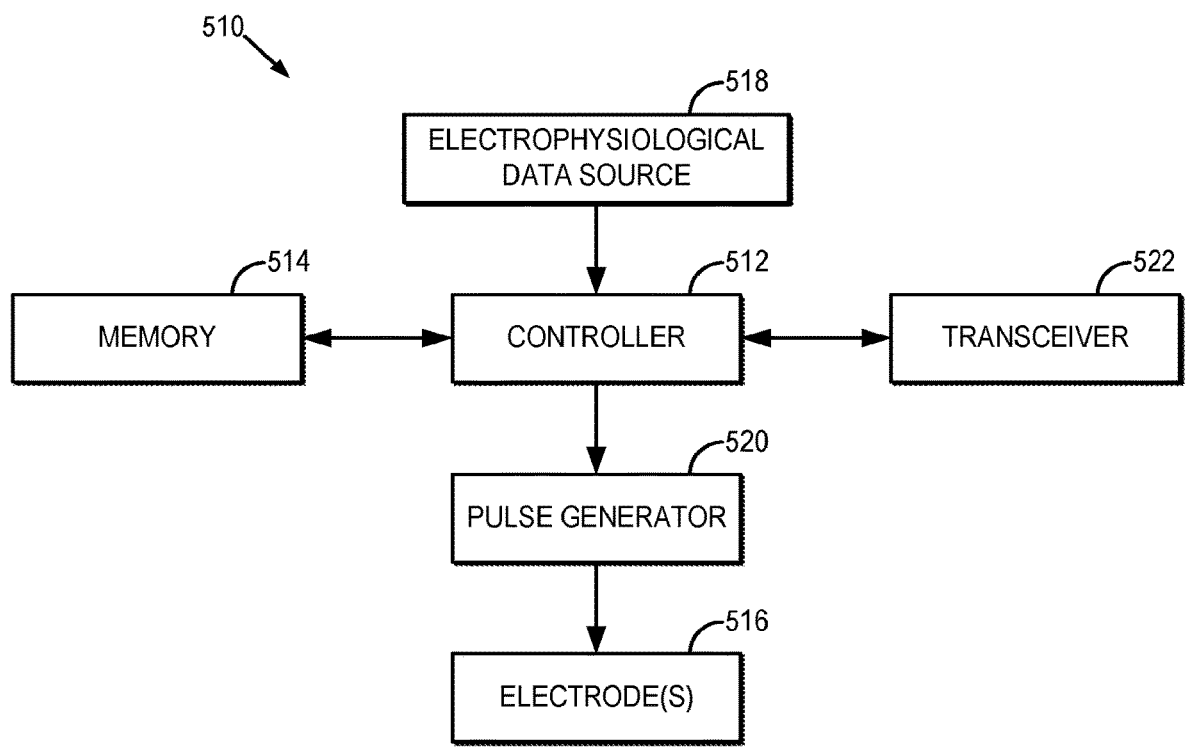
FIG. 5 is a block diagram of an example neuromodulation system that can implement methods described in the present disclosure.

Referring now to FIG. 5, an example neuromodulation system 510 that can implement the methods described above is illustrated. In general, the neuromodulation system 510 includes a controller 512, a memory 514, and at least one electrode 516. The neuromodulation system 510 can be implemented as an implantable medical device, such as an implanted electrical stimulation system, such as a neurostimulation system, which may include a deep brain stimulation ("DBS") system.

In some embodiments, at least one electrode 516 is capable of both sensing electrophysiological activity and delivering electrical stimulation. Thus, in these embodiments, the at least one electrode 516 also forms at least one sensor. An electrophysiological data source 518 provides electrophysiological data to the controller 512. The electrophysiological data may include electrophysiological signals measured from the EPN, or other data derived from the electrophysiological signals. As noted, in some implementations the electrophysiological data source 518 may include one or more electrodes 516 that are operating as sensing electrodes.

The controller 512 includes a processor to execute instructions embedded in or otherwise stored on the memory 514 to implement the methods described above. The memory 514 can also store electrophysiological data and other data for processing, as well as settings (e.g., stimulation parameters) to be provided to the controller 512 for directing the at least one electrode 516 to provide electrical stimulation to a subject.

At least one electrode 516 operates under control of the controller 512 to deliver electrical stimulations to the subject in response thereto. Processing circuitry in the controller 512 detects and processes electrophysiological data received by the electrophysiological data source 518 to determine the optimized stimulation parameters based on the methods and algorithms described above. The optimized stimulation parameters are provided as instructions to a pulse generator 520, which in response to the instructions provides an electrical signal to the at least one electrode 516 to deliver the electrical stimulations to the subject.

The neuromodulation system 510 can also include a transceiver 522 and associated circuitry for communicating with a programmer or other external or internal device. As one example, the transceiver 522 can include a telemetry coil.

In operation, the neuromodulation system 510 receives electrophysiological signals from the electrophysiological data source 518. These data are provided to the controller 512 where they are processed. The controller 512 analyzes the electrophysiological data and estimates therefrom optimal stimulation parameters, as described above. The optimized stimulation parameters are provided to the pulse generator 520 to control the at least one electrode 516 to generate electrical stimulation that will achieve the desired effect in the subject. As described above, in some implementations, electrophysiological signals are measured from the EPN, but electrical stimulation is provided to another anatomical location, such as locations in the hippocampus or other locations in the brain, spinal cord, central nervous system, peripheral nervous system, or other organ systems. Similarly, electrophysiological signals can be recorded from the other anatomical location with neuromodulation treatment being provided to the EPN.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating treatment plan data from images acquired using a magnetic resonance imaging (MRI) system, the method comprising:
   (a) accessing with a computer system, magnetic resonance image data acquired from a subject using an ultra-high field MM system, wherein the magnetic resonance image data comprise T2-weighted images of the subject;
   (b) localizing the subject's endopiriform nucleus (EPN) by using the computer system to analyze the T2-weighted images in the magnetic resonance image data, generating output as localized EPN data that indicate at least one of a spatial location and spatial extent of the subject's EPN;
(c) generating treatment plan data with the computer system using the localized EPN data, wherein the treatment plan data define a treatment delivery for delivering treatment to the subject's EPN.

2. The method as recited in claim 1, wherein analyzing the T2-weighted images comprises segmenting the T2-weighted images in order to localize the subject's EPN in the T2-weighted images.

3. The method as recited in claim 1, wherein the magnetic resonance image data further comprise at least one of T1-weighted images or proton density-weighted images, and wherein localizing the subject's EPN comprises analyzing the T2-weighted images in addition to the at least one of T1-weighted images or proton density-weighted images, generating output as the localized EPN data.

4. The method as recited in claim 3, wherein localizing the subject's EPN comprises segmenting the T2-weighted images using data from the at least one of T1-weighted images or proton density-weighted images to guide segmenting the T2-weighted images.

5. The method as recited in claim 1, wherein the magnetic resonance image data further comprise fiber tracking maps that depict white matter fiber tracks in the subject, and wherein localizing the subject's EPN comprises analyzing the T2-weighted images in addition to the fiber tracking maps.

6. The method as recited in claim 5, wherein localizing the subject's EPN comprises segmenting the T2-weighted images using data from the fiber tracking maps to guide segmenting the T2-weighted images.

7. The method as recited in claim 6, wherein using data from the fiber tracking maps to guide segmenting the T2-weighted images comprises identifying white matter fiber tracks adjacent the subject's EPN in the fiber tracking maps in order to separate the white matter fiber tracks from the subject's EPN.

8. The method as recited in claim 1, wherein the magnetic resonance image data comprise multislice T2-weighted images acquired with an interleaved acquisition to reduce interactions between spatially adjacent slices.

9. The method as recited in claim 1, wherein the treatment plan data comprise coordinate data that define coordinates of the localized EPN data in a coordinate system.

10. The method as recited in claim 9, wherein the coordinate data are stereotactic coordinate data and the coordinate system is a stereotactic coordinate system.

11. The method as recited in claim 9, wherein the coordinate system corresponds to a coordinate system for a surgical navigation system.

12. The method as recited in claim 1, wherein the treatment plan data comprise trajectory data that define one or more trajectories for delivering the treatment to the subject's EPN.

13. The method as recited in claim 12, wherein the one or more trajectories are generated by the computer system to avoid critical anatomical structures in the subject.

14. The method as recited in claim 1, wherein the treatment is a neuromodulation treatment.

15. The method as recited in claim 14, wherein the neuromodulation treatment implements electrical stimulation of the subject's EPN.

16. The method as recited in claim 15, further comprising designing an electrode lead design based on the localized EPN data, such that the electrode lead design is optimized for the subject's EPN.

17. The method as recited in claim 14, further comprising analyzing the magnetic resonance image data with the computer system to generate localized hippocampus data that identifies a location of the subject's hippocampus, and wherein the treatment plan data also define a data acquisition for measuring electrical signals from the subject's hippocampus contemporaneously with delivering the neuromodulation treatment to the subject's EPN.

18. The method as recited in claim 17, further comprising updating treatment delivery for delivering the neuromodulation treatment to the subject's EPN based on the electrical signals measured from the subject's hippocampus.

19. The method as recited in claim 14, further comprising analyzing the magnetic resonance image data with the computer system to generate localized spinal cord data that identifies a location in the subject's spinal cord, and wherein the treatment plan data also define a data acquisition for measuring electrical signals from the location in the subject's spinal cord contemporaneously with delivering the neuromodulation treatment to the subject's EPN.

20. The method as recited in claim 14, wherein the neuromodulation treatment is applied to the subject's hippocampus, and wherein the treatment plan data also define a data acquisition for measuring electrical signals from the subject's EPN contemporaneously with delivering the neuromodulation treatment to the subject's hippocampus.

21. The method as recited in claim 20, wherein the neuromodulation treatment comprises electrical stimulation of the subject's hippocampus.

22. The method as recited in claim 20, further comprising updating treatment delivery for delivering the neuromodulation treatment to the subject's hippocampus based on the electrical signals measured from the subject's EPN.

23. The method as recited in claim 14, wherein the neuromodulation treatment is applied to a location in the subject's spinal cord, and wherein the treatment plan data also define a data acquisition for measuring electrical signals from the subject's EPN contemporaneously with delivering the neuromodulation treatment to the location in the subject's spinal cord.

24. The method as recited in claim 23, wherein the neuromodulation treatment comprises electrical stimulation of the location in the subject's spinal cord.

25. The method as recited in claim 23, further comprising updating treatment delivery for delivering the neuromodulation treatment to the location in the subject's spinal cord based on the electrical signals measured from the subject's EPN.

26. The method as recited in claim 1, wherein the ultra-high field MM system has a magnetic field strength of at least 7 Tesla.

27. A neuromodulation device for implant in a brain of a subject, the neuromodulation device comprising:
a pulse generator configured to generate electrical pulses configured to be delivered the brain of the subject;
a controller coupled to receive data from a plurality of sources including at least one of localized endopiriform nucleus (EPN) data or a treatment plan generated from EPN data and configured to control the pulse generator to generate, using the EPN data, the electrical pulses in order to effectuate a therapy to control seizures in the subject, wherein the EPN data is formed from T2-weighted magnetic resonance images of the brain of the subject; and
an electrical lead comprising:
a distal-end region having a plurality of electrodes configured to extend into the brain of the subject to deliver the electrical pulses generated by the pulse generator to the brain of the subject; and a proximal-end region having a lead interface configured to mechanically and electrically couple to and subsequently decouple from the pulse generator.

* * * * *

UNITED STATES PATENT AND TRADEMARK OFFICE
CERTIFICATE OF CORRECTION

PATENT NO. : 12,082,905 B2
APPLICATION NO. : 17/766420
DATED : September 10, 2024
INVENTOR(S) : Thomas R. Henry et al.

It is certified that error appears in the above-identified patent and that said Letters Patent is hereby corrected as shown below:

In the Specification

Column 5, Line 53, "Bo" should be --$B_0$--.

In the Claims

Column 16, Claim 1, Line 61, "MM" should be --MRI--.

Column 18, Claim 26, Line 50, "MM" should be --MRI--.

Signed and Sealed this
Fifth Day of November, 2024

Katherine Kelly Vidal
*Director of the United States Patent and Trademark Office*